United States Patent [19]

Kimber et al.

[11] Patent Number: 5,059,539

[45] Date of Patent: Oct. 22, 1991

[54] TEST FOR CATALYST ACTIVITY

[75] Inventors: Geoffrey M. Kimber; Stephen T. Walton, both of Prestatyn, Wales

[73] Assignee: Coal Industry (Patents) Limited, United Kingdom

[21] Appl. No.: 390,898

[22] Filed: Aug. 8, 1989

[30] Foreign Application Priority Data

Aug. 11, 1988 [GB] United Kingdom ............... 8819055

[51] Int. Cl.$^5$ ............................................. G01N 31/10
[52] U.S. Cl. ........................................ 436/37; 436/34; 436/140
[58] Field of Search ............... 436/34, 37, 140, 2; 208/419, 107, 134, 143; 585/250, 263, 266, 654, 700

[56] References Cited

U.S. PATENT DOCUMENTS

| | | | |
|---|---|---|---|
| 3,267,026 | 8/1966 | Decker | 436/37 X |
| 3,541,169 | 11/1970 | Hicks et al. | 260/667 |
| 4,334,977 | 6/1982 | Derbyshire et al. | 208/416 |
| 4,837,158 | 6/1989 | Toulhoat et al. | 436/37 |

FOREIGN PATENT DOCUMENTS 0411371  5/1974  U.S.S.R. ............................... 436/37
2104546  3/1983  United Kingdom .

*Primary Examiner*—David L. Lacey
*Assistant Examiner*—Jeffrey R. Snay
*Attorney, Agent, or Firm*—Stevens, Davis, Miller & Mosher

[57] ABSTRACT

A method is provided for testing the activity of a catalyst for a chemical reaction in which naphthalene is reversibly hydrogenated by gaseous hydrogen into tetralin, which avoids the need to pressurize a test vessel with hydrogen, enables simple apparatus to be used and gives good accuracy. Tetralin and catalyst are introduced into a sealed container, the container is heated to a reaction temperature for a predetermined time, and the amount of naphthalene formed by dehydrogenation is determined. The method is applicable to the measurement of catalyst activity for catalysts used in the production by hydrogenation of coal-derived liquids.

7 Claims, 3 Drawing Sheets

TEST FOR CATALYST ACTIVITY

This invention relates to a method of testing a heterogeneous or homogeneous catalyst used in a reversible hydrogenation reaction e.g. for the production of coal derived liquids in order to measure the hydrogenation activity of said catalyst.

At the Wilsonville advanced coal liquefaction research and development facility the hydrogenation activity of the above catalysts has been measured directly. Naphthalene was hydrogenated directly in the presence of the catalyst and in a small stirred autoclave to yield tetralin and decalin. Gas-liquid chromatography (GLC) was used to measure the conversion of naphthalene to these products, and from this information the hydrogen consumption was calculated. This consumption was then used to calculate a function related to catalyst activity. But the Wilsonville test suffers from a number of disadvantages which it is an object of this invention to remedy. Firstly the autoclave has to be pressurised with hydrogen, typically to 1000 psi. which carries with it an inherent risk of explosion in the event of rupture of the autoclave consequent upon structural failure. For this reason the Wilsonville autoclave when assembled is heavy and expensive. It has to be immersed in a large sand bath during heating and an air pneumatic lifter is required to enable the autoclave to be lifted from and returned into the sand bath. Secondly the pressure of hydrogen at the outset of the test has to be measured to enable the catalyst activity to be calculated, and error in measuring hydrogen pressure introduces error in the measured catalyst activity. Thirdly, because of variable recovery of product and of unreacted starting materials from the bomb, material balances in tests carried out using the Wilsonville bomb of from 90 to 104% have been reported, and such inaccuracies could only have helped to compound errors in the measured catalyst activity.

It is therefore an object of the invention to provide a test for the activity of a hydrogenation catalyst that does not require an initial pressurisation with hydrogen, can be carried out in a small apparatus of simple construction, and enables accurate material balances to be recorded in the test.

This problem has been solved, according to the invention for the case of a reversible hydrogenation reaction.

Accordingly there is provided a method of testing the activity of a catalyst for a chemical reaction in which a starting material is reversibly hydrogenated by gaseous hydrogen into a reaction product, which comprises introducing material which is chemically the same as the reaction product and catalyst into a sealed container, heating the container to a reaction temperature for a predetermined time, and determining the amount of a material that is chemically the same as the starting material and is formed by dehydrogenation.

The terms "starting material" and "reaction product" as used herein in relation to the test method refer to the chemical identity of the materials formed by and/or used for the test, and not necessarily to the method by which the test materials have been made.

The starting material of the overall reaction is typically an aromatic hydrocarbon and the reaction product is then a hydroaromatic hydrocarbon or a saturated hydrocarbon. Thus the hydroaromatic or saturated hydrocarbon and the catalyst only are present in the sealed container at the start of the test, and the production of the aromatic hydrocarbon is measured.

A test according to the invention preferably makes use of the equilibrium that exists between tetralin and naphthalene:

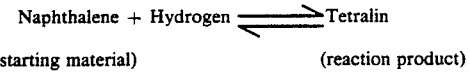

(starting material)    (reaction product)

(wherein $K_1$ represents the rate constant for the forward reaction and $K_2$ represents the rate constant for the reverse reaction). The catalyst lowers the energy barrier to both the forward reaction ($K_1$) and the reverse reaction ($K_1$), increasing the rate of both reactions, i.e. increasing both $K_1$ and $K_2$. The relative values of the rate constant $K_2$ for the reverse reaction using different catalyst samples is consequently related to the relative values for the rate constant $K_1$ for the forward reaction. In this way, changes in hydrogenation activity (related to $K_1$) can be measured by measuring functions related to $K_2$.

In practice tetralin together with the catalyst to be tested is introduced into a small unstirred autoclave. No hydrogen is added to the autoclave. The autoclave is heated to an elevated temperature, and the tetralin dehydrogenates as the equilibrium shifts towards a new value characteristic of the elevated temperature used. The rate at which the system moves towards equilibrium and hence the quantity of naphthalene produced in a given time depends upon the activity of the catalyst. The quantity of naphthalene produced is determined by GLC or by $^1$H-nuclear magnetic resonance ($^1$H-nmr). The quantity of naphthalene produced is then expressed as a percentage of that produced when using a fresh unused catalyst to obtain a measure of the catalyst activity.

with percent naphthalene on the ordinate and time on the abscissa, wherein y = naphthalene produced from fresh catalyst
x = naphthalene produced from used catalyst
z = naphthalene present in a blank run.

Figure 1:
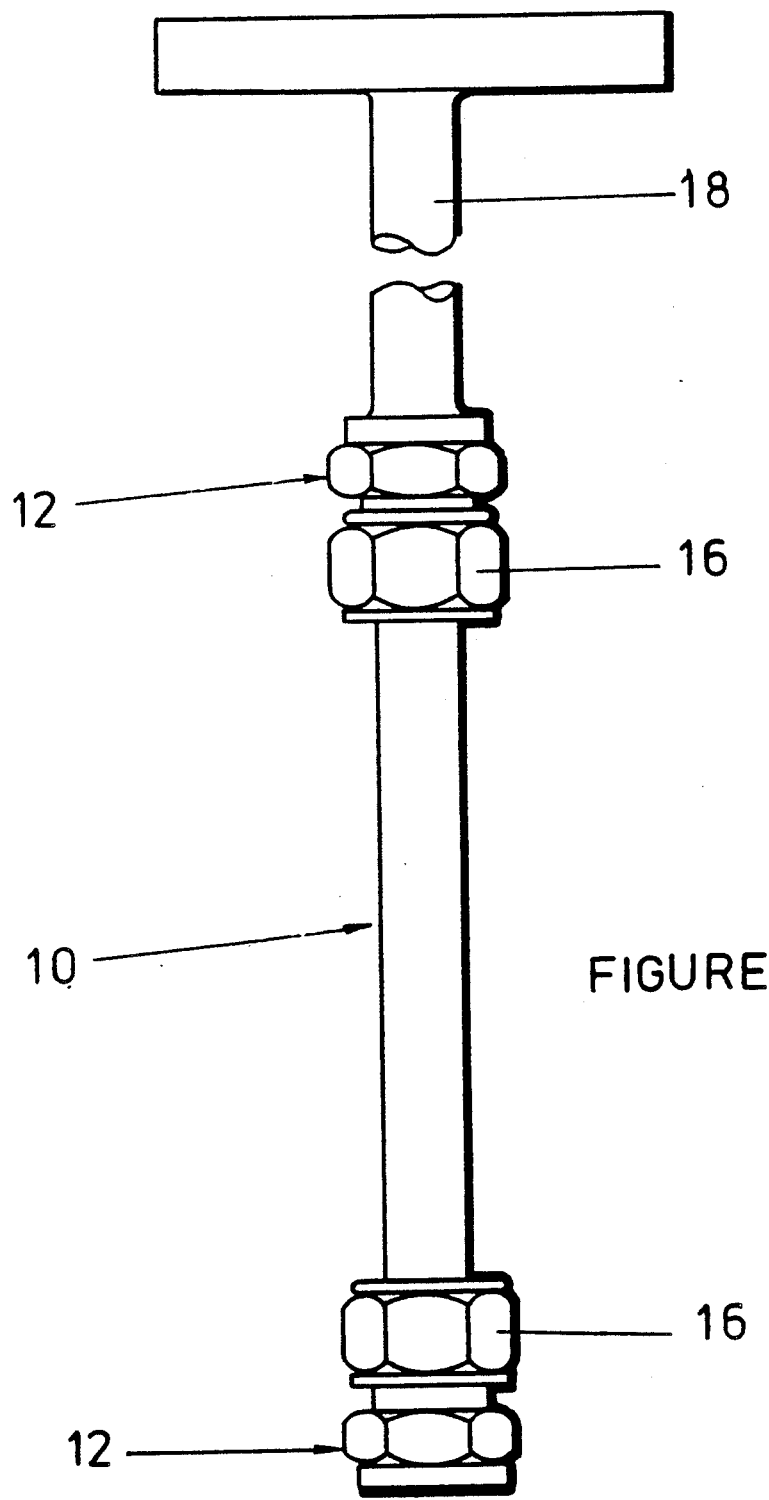
FIG. 1 is a schematic elevation view of an autoclave which can be used to carry out a test according to the invention.

An autoclave that can be used to carry out a test according to the invention is shown in elevation in FIG. 1. It comprises a thin tubular barrel 10 closeable at each end by means of a capped compression fitting such as Gyrolock cap 12 which is attached by means of a compression fitting 16. One of the caps 12 is attached to a handle or T-support arm 18. A predetermined quantity (e.g. 2g) of Tetralin and a predetermined quantity of catalyst are charged into the autoclave or bomb. When extrudate catalysts are being tested, the nominal length of the catalyst may conveniently be 70 mm. Its crosssection is known, and hence its cylindrical area is also known. For a fresh catalyst, the 70 mm nominal length corresponds to a weight of about 0.2 g for a catalyst of 1.5 mm nominal diameter. Both the mass of the catalyst taken and a function of its area are therefore known. The caps 12 are then tightened to completely seal the autoclave.

For measurement of catalyst deactivation, four such bombs are prepared in this way for the fresh unused catalyst and three of the used catalyst whose activity is to be measured. Each autoclave is then heated to a reaction temperature within a small temperature band which is itself within the range 543k to 693k, the exact choice of the band being matched to the catalyst. The experimental procedure is as follows. A thermocouple is attached to the exterior of the autoclave, and the assembly is then immersed in a sand bath for a precisely measured time period e.g. twenty minutes and during that time is suspended from and gently shaken by a flask shaker. After the time period has expired, the bomb is immediately taken from the sand bath and quenched in a bucket of cold water. The above procedure is repeated for a number of fresh catalyst samples and for a number of used catalyst samples at temperatures dispersed as evenly as possible over the above mentioned temperature band. The reaction products are recovered from each autoclave and the percentage of naphthalene is determined by GLC or NMR.

Figure 2:
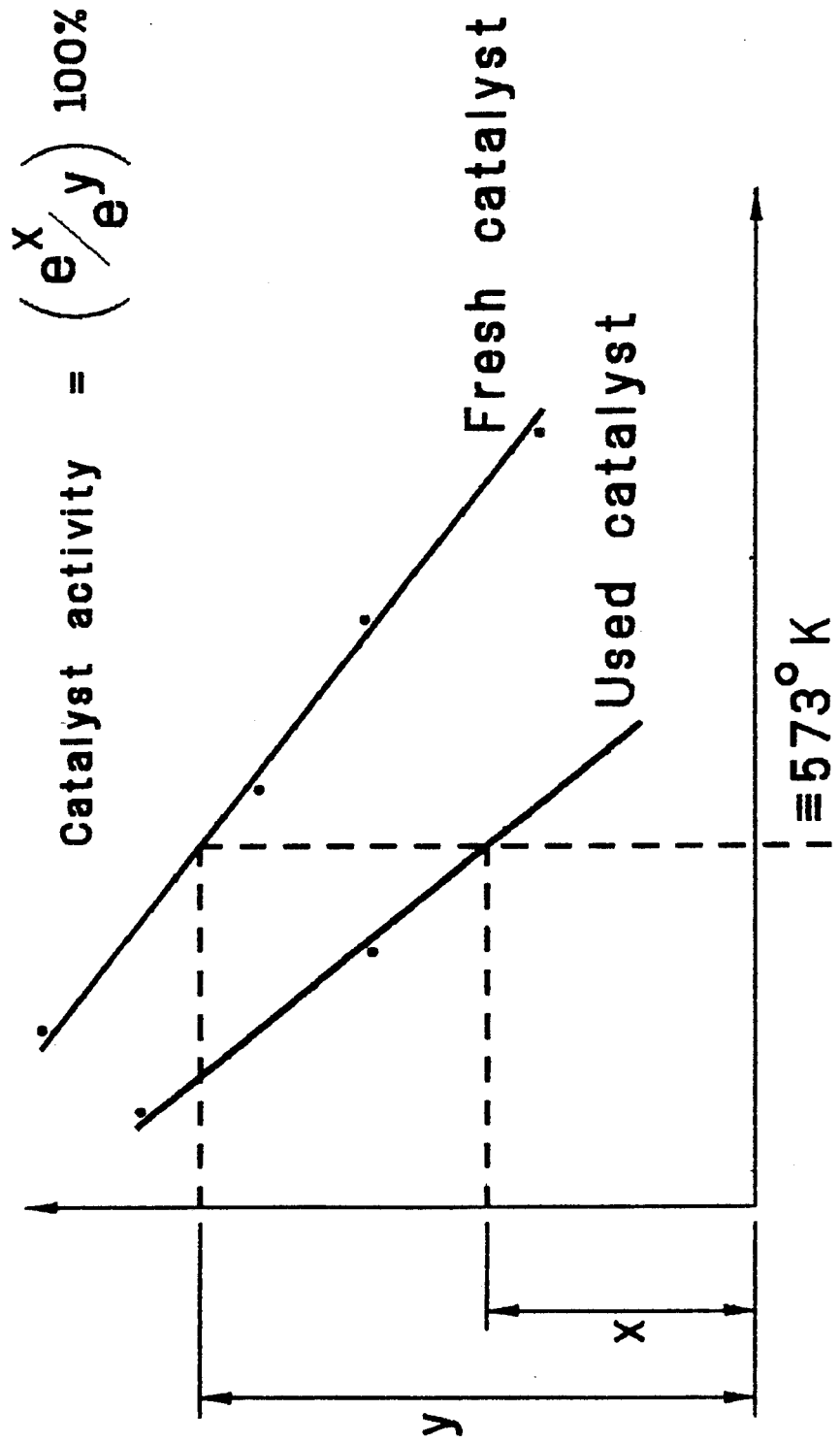
FIG. 2 is a graph plotting the log % of naphthalene on the ordinate versus $10^3T$ on the abscissa.

For interpretation of the resulting measurements, the loge of the % naphthalene corrected to a standard catalyst quantity is then plotted against 1000/T where T represents the test temperature of an individual autoclave in °K for both the fresh and used catalyst. Two straight line graphs are obtained as in FIG. 2, one for the fresh catalyst and one for the used catalyst, and the log % naphthalene may be found by interpolation for both the fresh and the used catalyst at a standard temperature. The catalyst activity is then expressed as:

$$100 \times \% \text{ naphthalene for used catalyst naphthalene for fresh catalyst}$$

Figure 3:
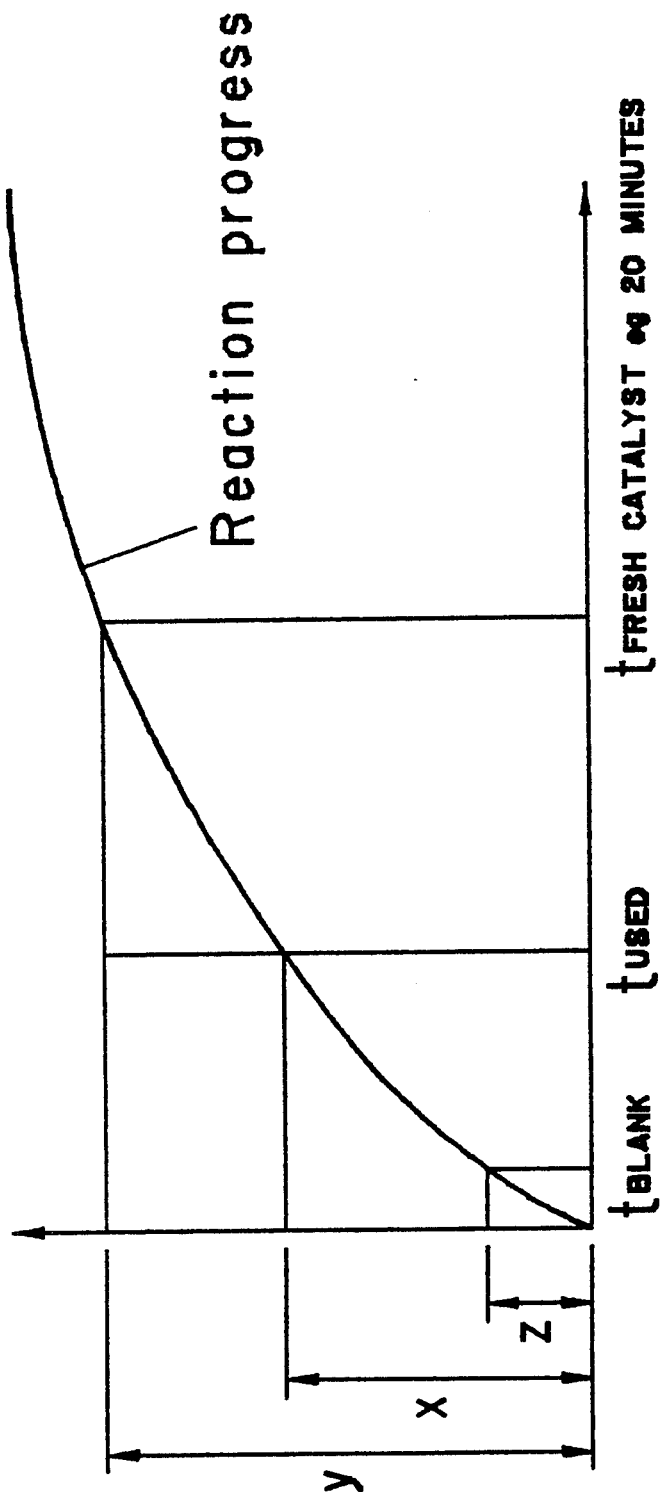
FIG. 3 is a graph plotting the catalyst activity function $$\left( \frac{t_{used} - t_{blank}}{t_{fresh} - t_{blank}} \right) \times 100;$$

Alternatively, a catalyst activity function may be found which relates the movement of the system towards equilibrium for the fresh catalyst with that of the used catalyst in terms of time. FIG. 3 of the accompanying drawings illustrates the manner in which catalyst activity is calculated on a time basis.

It will be appreciated that the above procedure has significant advantages in that the autoclave or bomb used can be made of simple metal tube closed by end caps, the reason being that no hydrogen is charged from the outset and the autoclave has only to withstand the pressure of the relatively small amount of hydrogen evolved in the dehydrogenation reaction. Material recovery is considerably easier, and material balances of 99.9% have been achieved, eliminating errors due to variable recovery from the bomb.

What is claimed is:

1. A method of testing the activity of a reversible hydrogenation catalyst for promoting a given chemical reaction in which a starting material is reversibly hydrogenated by gaseous hydrogen into a reaction product, which comprises the steps of introducing a hydrogenated material that is chemically the same as the reaction product of the given chemical reaction, and a reversible hydrogenation catalyst into a sealed container, heating the container too a reaction temperature for a predetermined time effecting dehydrogenation of said hydrogenated material to yield a dehydrogenated product which is chemically the same as the starting material of the given chemical reaction, determining the amount of said dehydrogenated product that is chemically the same as the starting material of the given chemical reaction, and has formed by dehydrogenation, determining the activity of said catalyst for promoting dehydrogenation of said dehydrogenated material, and correlating said activity of said catalyst for promoting the dehydrogenation of said hydrogenated material to the activity of said catalyst for promoting hydrogenation of said dehydrogenated product which is chemically the same as the starting material of the given chemical reaction.

2. A method according to claim 1, wherein said dehydrogenated product which is chemically the same as the starting material is an aromatic hydrocarbon and said hydrogenated material which is chemically the same as the reaction product is a hydroaromatic hydrocarbon.

3. A method according to claim 2, wherein said dehydrogenated product is naphthalene and said hydrogenated material is tetralin.

4. A method according to claim 1, wherein said catalyst is a homogeneous catalyst.

5. A method according to claim 1, wherein said catalyst is a heterogeneous catalyst.

6. A method according to claim 1, wherein said catalyst is effective for the production of coal-derived liquids by hydrogenation.

7. A method according to claim 1, wherein the step of determining the activity of said catalyst for promoting dehydrogenation of said hydrogenated material comprises first measurements made with fresh catalyst and second measurements made with used catalyst.

* * * * *